US006306114B1

(12) United States Patent
Freeman et al.

(10) Patent No.: US 6,306,114 B1
(45) Date of Patent: Oct. 23, 2001

(54) VALVED CANALICULAR PLUG FOR LACRIMAL DUCT OCCLUSION

(75) Inventors: C. Curtis Freeman, Cordova, TN (US); Nicholas J. Webb, Wrightwood, CA (US)

(73) Assignee: Eagle Vision, Inc., Memphis, TN (US)

( * ) Notice: Subject to any disclaimer, the term of this patent is extended or adjusted under 35 U.S.C. 154(b) by 0 days.

(21) Appl. No.: 09/098,234

(22) Filed: Jun. 16, 1998

(51) Int. Cl.[7] ............... A61M 5/00; A61F 2/02; A61B 17/00
(52) U.S. Cl. ................. 604/9; 604/8; 128/887; 623/11
(58) Field of Search ................. 604/8–10, 289, 604/290, 294, 298, 516, 523, 537; 128/887; 623/11, 12, 14; 606/192, 194

(56) References Cited

U.S. PATENT DOCUMENTS

| 3,949,750 | 4/1976 | Freeman ................ 128/260 |
| 4,886,488 | 12/1989 | White ........................ 604/9 |
| 4,915,684 | * 4/1990 | MacKeen et al. ........... 604/8 |
| 4,959,048 | 9/1990 | Saeder et al. .............. 604/9 |
| 5,171,270 | 12/1992 | Herrick ..................... 623/11 |
| 5,224,938 | 7/1993 | Fenton, Jr. ............... 604/247 |
| 5,283,063 | 2/1994 | Freeman .................. 424/427 |
| 5,334,137 | 8/1994 | Freeman .................... 604/8 |
| 5,417,651 | 5/1995 | Guena et al. ............... 604/8 |
| 5,423,777 | 6/1995 | Tajiri ....................... 604/294 |
| 5,601,553 | 2/1997 | Trebing et al. ............. 606/61 |
| 5,626,559 | * 5/1997 | Solomon .................... 604/9 |
| 5,645,565 | 7/1997 | Rudd et al. ............... 606/213 |
| 5,807,303 | * 9/1998 | Bays ......................... 604/9 |
| 5,830,171 | * 11/1998 | Wallace ..................... 604/8 |
| 6,016,806 | * 1/2000 | Webb ...................... 128/846 |

FOREIGN PATENT DOCUMENTS

| 2069339A | 8/1981 | (GB) . |
| 2160778A | 1/1986 | (GB) . |

* cited by examiner

Primary Examiner—William E. Kamm
Assistant Examiner—Patricia Bianco
(74) Attorney, Agent, or Firm—David P. Gordon; David S. Jacobson; Thomas A Gallagher (57) ABSTRACT

A canalicular plug includes a throughbore provided with a valve. Preferably, the plug has a proximal occluding head, a central shaft and a distal body portion. The throughbore is preferably stepped and includes a large proximal portion for receiving an insertion tool and a smaller distal portion. The valve is preferably integrally molded with the canalicular plug, and the plug is preferably made from a resilient biocompatible material. According to a preferred aspect of the invention, the distal body portion includes at least one slot dividing the distal portion into a plurality of resilient portions which are biased apart and coupled by a foldable curtain portion extending between the resilient portions. The resilient portions are inwardly compressible about the slot. When compressed together, the distal ends of the resilient portions together form a generally conical or frustoconical shape which facilitates insertion through the punctal opening.

26 Claims, 8 Drawing Sheets

VALVED CANALICULAR PLUG FOR LACRIMAL DUCT OCCLUSION

BACKGROUND OF THE INVENTION

1. Field of the Invention

This invention relates broadly to medical canalicular inserts. More particularly, this invention relates to canalicular plugs which are placed into the punctal opening or the lacrimal duct to prevent lacrimal fluid from flowing through the lacrimal duct.

2. State of the Art

A variety of eye problems are related to an insufficient volume of tears on the surface of the eyes. The most common is keratoconjunctivitis sicca, also known as dry eyes. Contact lens problems are also often provoked by a lack of tear volume. A common cause for the insufficient tear volume is the drainage of tear fluid through the punctal opening of the nasal lacrimal duct and into the nasal passage, thereby removing the fluid from where it is needed at the eye surface. Furthermore, drainage of tear fluid through the nasal lacrimal duct into the nasal passage is believed to be the cause or associated with several additional problems such as post nasal drip, sinusitis, allergies, headaches, and snoring.

A number of methods for closing the punctal opening have been used to prevent drainage of tears through the nasal lacrimal duct, including suturing, laser sealing, and plugging. Plugging with a canalicular plug, such as a punctum plug or a lacrimal plug, is the least severe solution, is relatively inexpensive, and is being performed with increasing frequency.

Figure 25:
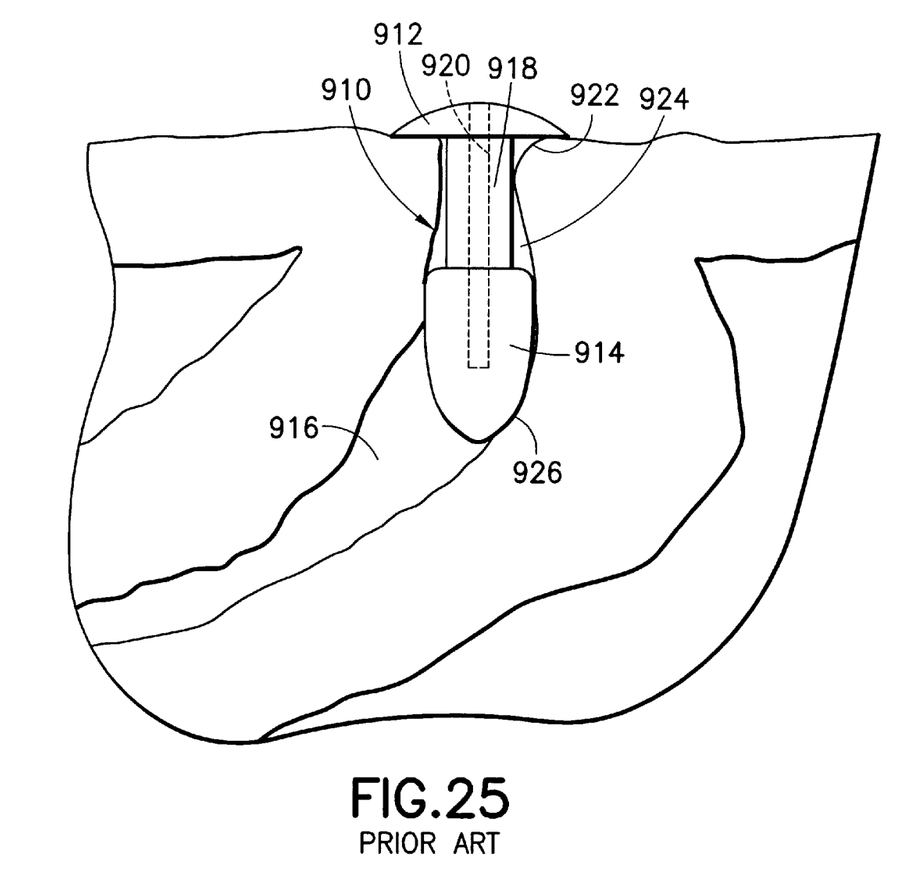
FIG. 25 is a side elevation of an implanted prior art punctum plug.

Referring to prior art FIG. 25, a punctum plug 910 typically is an elongate member having a proximal head 912, a relatively larger distal body 914 for occluding the lacrimal duct 916, and a relatively narrower rigid shaft 918 therebetween. The plug is usually provided with a proximal axial bore 920 for receiving a cylindrical insertion tool. In the punctum plug insertion procedure, an insertion tool is positioned into the bore 920 of the plug, the body of the plug is directed at the punctal opening 922 of the lacrimal duct 916, and force is applied to the insertion tool to move the body 914 of the plug through the punctal opening 922 and into the vertical puncta 924 and lacrimal duct 916. Once the plug is in the vertical puncta and lacrimal duct, the insertion tool is removed. The plug is fully inserted when the head seats against the tissue at the punctal opening and the body seats within the lacrimal duct so as to block the passage of tear fluid and thereby retain tear fluid at the surface of the eye. Similarly, lacrimal plugs which seat entirely within the lacrimal duct (and below the punctal opening) are also known.

It has been found that prior art punctum and lacrimal plugs, while providing some benefit often do not provide satisfactory occlusion of the lacrimal duct. Tear fluid tends to flow through the interstices between the body of the plug and the tissue of the vertical puncta of the nasal lacrimal duct. One proposed prior art solution of this problem has been to provide an enlarged distal body to the plug. However, the larger distal body is difficult to insert through the relatively small punctal opening.

In addition, with prior art canalicular plugs, completely occluding the lacrimal duct can provoke other detrimental effects. For example, when a patient has a plug implanted in his or her lacrimal duct, simple acts such as sneezing or nose blowing can cause a momentary pressure differential to occur about the plug. That is, referring to prior art FIG. 25, the lacrimal duct 916 on the body side of the plug (below body 914) is subject to increased pressure relative to the head side of the plug (above head 914). This pressure differential can result in the plug being forced up and inadvertently dislodged from the puncta. Other activities, such as eye rubbing and ear-popping (e.g., after scuba diving or flying) can similarly cause a pressure differential and result in inadvertent expulsion of the plug from the lacrimal duct.

SUMMARY OF THE INVENTION

It is therefore an object of the invention to provide a canalicular plug which occludes the flow of tears through the lacrimal duct.

It is another object of the invention to provide a canalicular plug which prevents a pressure differential from occurring about the proximal and distal ends of the plug and, as such, is not readily subject to unintentional dislodgement from the lacrimal duct.

It is also an object of the invention to provide a canalicular plug which is designed to facilitate insertion into the lacrimal duct.

In accord with these objects which will be discussed in detail below, a canalicular plug is provided which generally includes a proximal head, a distal body, and a shaft between the head and the body. The plug has a throughbore provided with a valve. The throughbore is preferably stepped, having a relatively larger proximal portion for receiving an insertion tool and a relatively smaller distal portion provided with the valve. The plug is preferably made from a resilient biocompatible material, and the valve is preferably integrally molded with the plug and designed to open only when subject to a relatively large pressure differential across the plug.

According to a preferred embodiment of the invention, the distal portion of the canalicular plug includes at least one slot dividing the distal portion into a plurality of resilient portions which are biased apart, yet inwardly compressible about the slot. When compressed together, the distal ends of the resilient portions together form a generally conical or frustoconical shape which is smaller in cross-sectional area than the non-compressed body portion, and thereby facilitates insertion. The body includes at least one foldable pleat which uninterruptingly connects the upper and peripheral areas of the resilient portions together.

Once the plug is seated in the lacrimal duct, the head and body portions occlude the passage of tear fluid therethrough. The valve prevents tear fluid from passing from the eye through the stepped throughbore and into the lacrimal duct. However, when pressure builds up within the lacrimal duct, e.g., because of sneezing, ear popping, etc., the valve opens, thereby permitting the pressure to equalize and preventing the plug from dislodging. According to particular embodiments of the invention, the valve is preferably a flapper valve, a duck bill valve, or a slit valve, although other valve-types can be used.

According to additional embodiments, the canalicular plug has either a compressible proximal head and a shaft provided with a valve, or a shaft provided with a valve and a relatively larger body portion. In both additional embodiments, the canalicular plug is adapted for relatively deeper lacrimal duct insertion.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
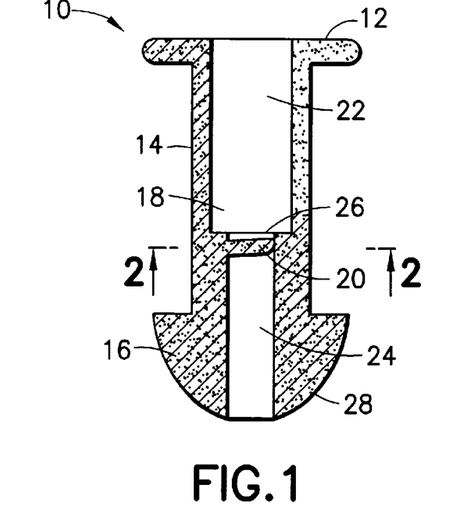
FIG. 1 is a section view of a valved canalicular plug according to a first embodiment of the invention, with the valve being shown in a closed position.
Figure 2:
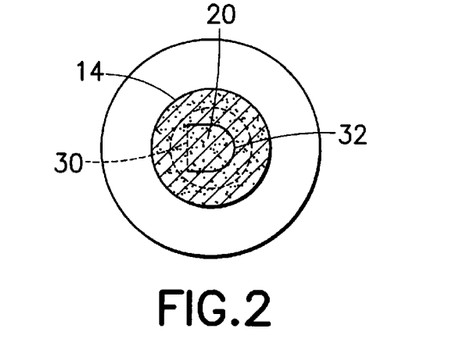
FIG. 2 is a cross-section through line 2—2 in FIG. 1 showing a first embodiment of a valve in the valved canalicular plug of the invention, the valve being shown in a closed position.
Figure 3:
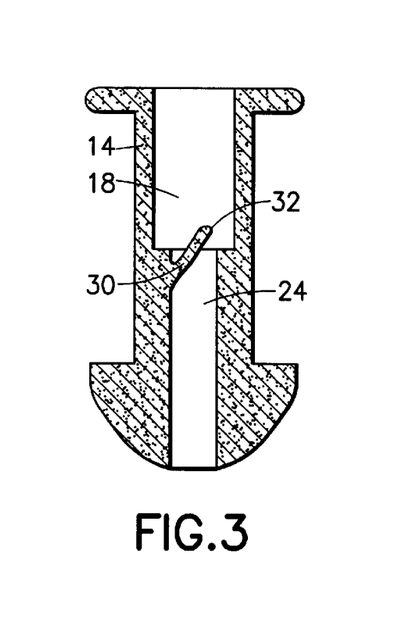
FIG. 3 is a view similar to FIG. 1, with the valve being shown in an open position.

Turning now to FIG. 1, a first embodiment of a canalicular plug 10 according to the invention is shown. The canalicular plug 10 generally includes a proximal head 12, a distal body 16, and a shaft 14 provided between the head 12 and the body 16. The plug 10 defines an axial throughbore 18 extending through the head 12, the shaft 14, and the body 16. A valve 20, described below, is provided in the axial throughbore. Preferably, the plug 10 is made from silicone or another soft, low durometer biocompatible material, by liquid injection molding, cast molding, or transfer molding.

More particularly, the axial throughbore 18 is preferably a stepped throughbore having a larger proximal portion 22 and a relatively smaller distal portion 24. The larger proximal portion 22 is sized to receive an insertion tool. An inner seat 26 which acts as a stop for the insertion tool is provided at the intersection of the proximal and distal portions 22, 24.

The head 12 preferably has a larger cross-sectional area than the body 16 such that the head 12 will not enter the punctal opening. The body 16 preferably has a generally conical or frustoconical shape with a distal surface 28 angled relative to the shaft 14. The conical body 16 eases movement of the punctal plug into the punctal opening.

Figure 8:
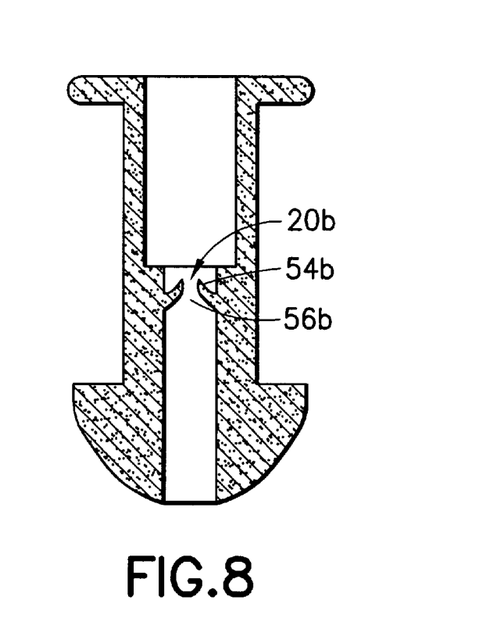
FIG. 8 is a view similar to FIG. 1 showing the third embodiment of the valve in an open position.

The valve 20 is preferably provided in the relatively smaller distal portion 24 of the axial throughbore 18, and preferably located adjacent the intersection of the proximal and distal portions 22, 24 of the throughbore 18. According to one embodiment of the invention, the valve 20 is a flapper valve having a hinged end 30 which is resiliently coupled to the plug, and a free end 32. The valve 20 is designed to require sufficient pressure to open such that tear build-up over the valve will not cause the valve to open downward, but the high pressure associated with a sneeze, ear popping, or eye rubbing will enable the free end 32 of the valve to open upward as shown in FIG. 8. When the valve 20 opens, an unobstructed passage is provided through the axial throughbore 18 of the plug to permit pressure about the plug to equalize.

Figure 4:
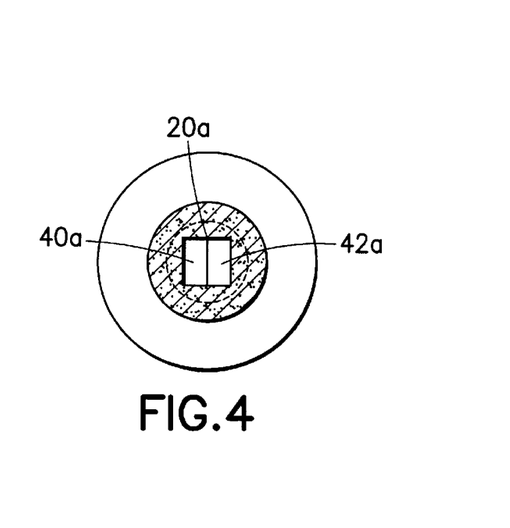
FIG. 4 is a view similar to FIG. 2 showing a second embodiment of a valve in the valved canalicular plug of the invention, the valve being shown in a closed position.
Figure 5:
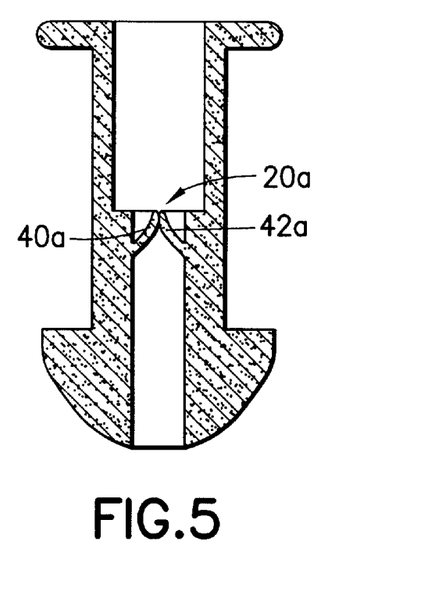
FIG. 5 is a view similar to FIG. 1 showing the second embodiment of the valve in a closed position.
Figure 6:
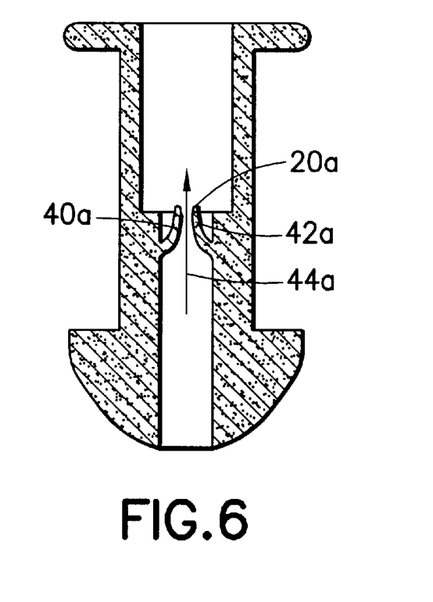
FIG. 6 is a view similar to FIG. 5 showing the second embodiment of the valve in an open position.

It will be appreciated that other types of valves can be used in place of a flapper valve. Referring to FIGS. 4 and 5, a duckbill valve 20a is shown. The duckbill valve 20a comprises two resilient flaps 40a, 42a which are biased together. When fluid pressure is provided on the head side of the plug (in the form of tear fluid collected in the axial throughbore) the valve 20a is secured shut. However, as shown in FIG. 6, when relatively higher pressure (shown by arrow 44a) is provided on the body side of the plug, flaps 40a, 42a separate to open the valve 20a and provide an unobstructed passage through the axial throughbore.

Figure 7:
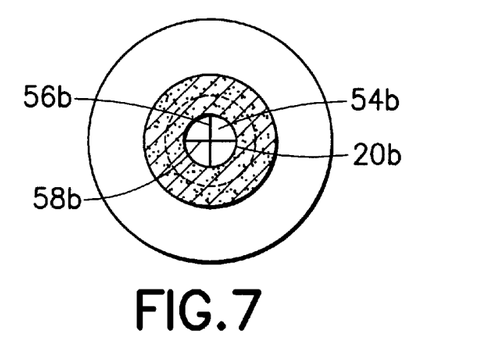
FIG. 7 is a view similar to FIG. 2 showing a third embodiment of a valve in the valved canalicular plug of the invention, the valve being shown in a closed position.

Turning to FIGS. 7 and 8, a slit valve 20b formed by a resilient membrane 54b having two preferably perpendicular slits 56b, 58b provided therein is shown. The membrane 54b is able to bend upward in the direction of the head (FIG. 8) when subject to relatively high lacrimal pressure, and then, due to the memory of the material, will return to its closed configuration. Regardless of the type of valve used in the plug, the valve should substantially prevent tear fluid from passing through the axial bore of the plug in the direction from head to body but should open when subject to relatively high pressure in the opposite direction.

Figure 9:
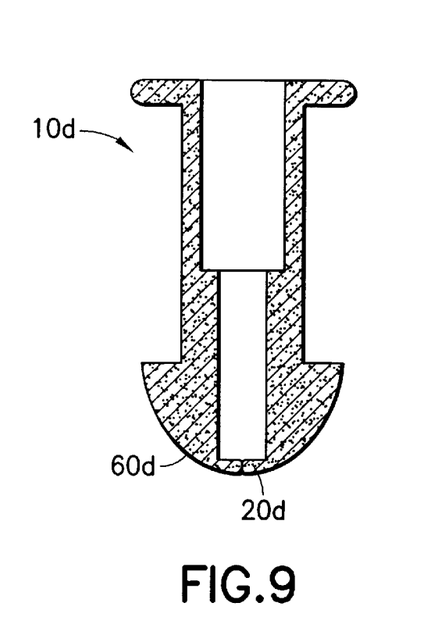
FIG. 9 is a section view of a valved canalicular plug according to a second embodiment of the invention.
Figure 10:
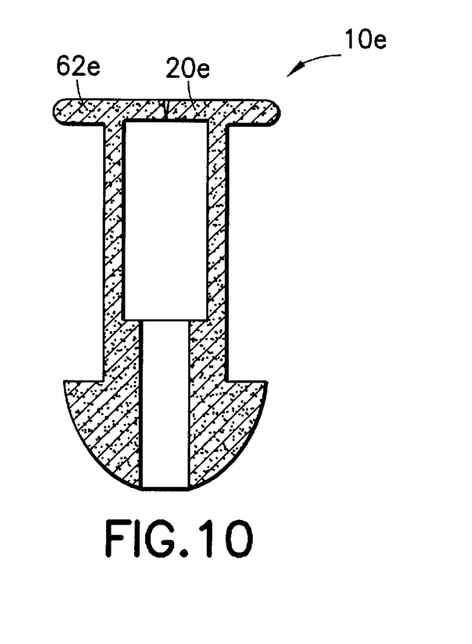
FIG. 10 is a section view of a valved canalicular plug according to a third embodiment of the invention.

It will also be appreciated that while it is preferabe to locate the valve at a somewhat central location within the axial throughbore 18, it will be appreciated that according to a second embodiment of the invention, the valve 20d may be provided at the distal end 60d (FIG. 9). Such an arrangement is particularly suited to ease of manufacture. Similarly, according to a third embodiment of the invention, the valve 20e may be provided at the proximal end 62e of the plug 10e (FIG. 10). Where the valve is provided at the proximal end of the plug, it will be appreciated that during plug insertion, which is described in detail below, an insertion tool may be forcibly passed through the valve and into the proximal portion of the throughbore. The resilient nature of the valve will permit the valve to retake shape once the insertion tool is removed.

Figure 11:
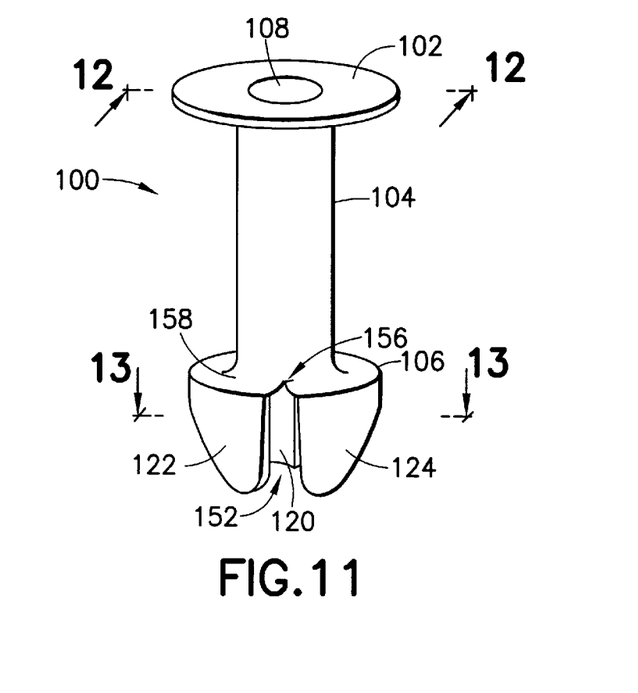
FIG. 11 is a perspective view of a fourth embodiment of a valved canalicular plug according to the invention.
Figure 12:
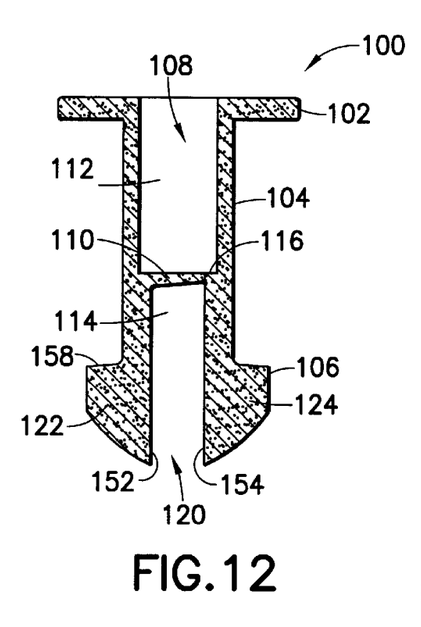
FIG. 12 is a section view through line 12—12 in FIG. 11.
Figure 13:
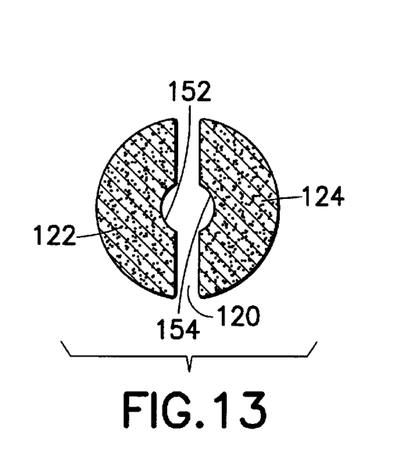
FIG. 13 is a cross-section view through line 13—13 in FIG. 11.

Turning now to FIGS. 11 through 13, and according to a presently preferred fourth embodiment of the invention, the plug 100 is generally configured as in the first embodiment, with a proximal head 102, a central shaft 104, and a distal body 106. An axial throughbore 108 extends from the head 102 through the shaft 104 and body 106, and a valve 110, as described above, is provided in the axial throughbore 108. The axial throughbore 108 is stepped, having a larger proximal portion 112 and a relatively smaller distal portion 114, and an inner seat 116 provided at the intersection of the proximal and distal portions 112, 114. The larger proximal portion 112 is sized to receive an insertion tool.

The distal end of the body 106 is split with a preferably diametrical longitudinal slot 120 which divides the distal end of the body into two preferably resilient longitudinal portions 122, 124. Each longitudinal portion 122, 124 is provided with a groove, 152 and 154 respectively, with the grooves 152, 154 together comprising the distal portion of the throughbore 114 (FIG. 13). An upper flexible pleat 156 is provided between the proximal portions of the longitudinal portions 122, 124 in order to couple the portions 122, 124 together. In this manner, the proximal surface 158 of the conical body 106 provides no entry into the distal portion 114 of the throughbore 108 and, despite the longitudinal slot 120, creates a barrier to the passage of tear fluid.

Figure 14:
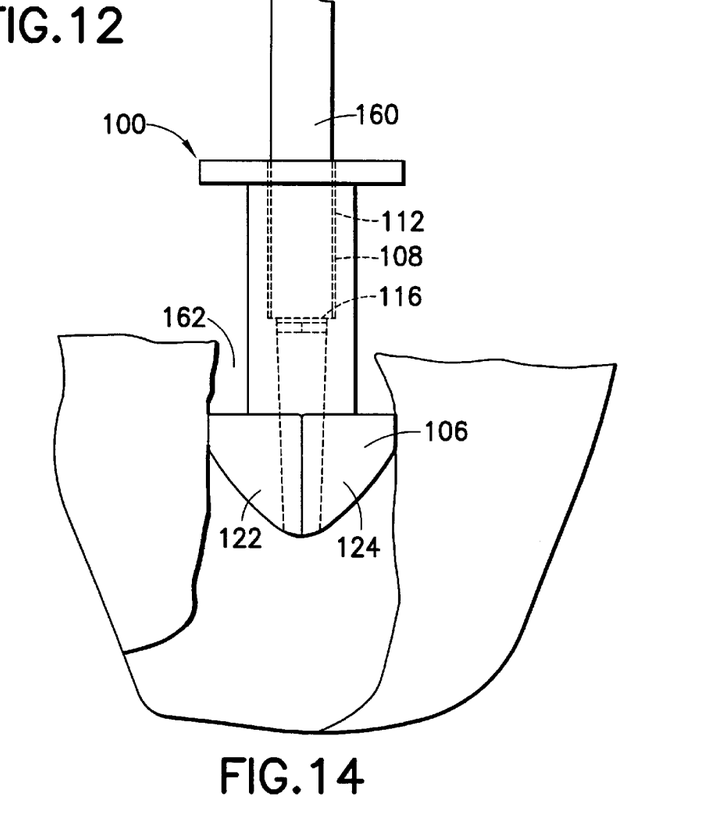
FIGS. 14 and 15 illustrate the insertion of the canalicular plug of the invention into the lacrimal duct.
Figure 15:
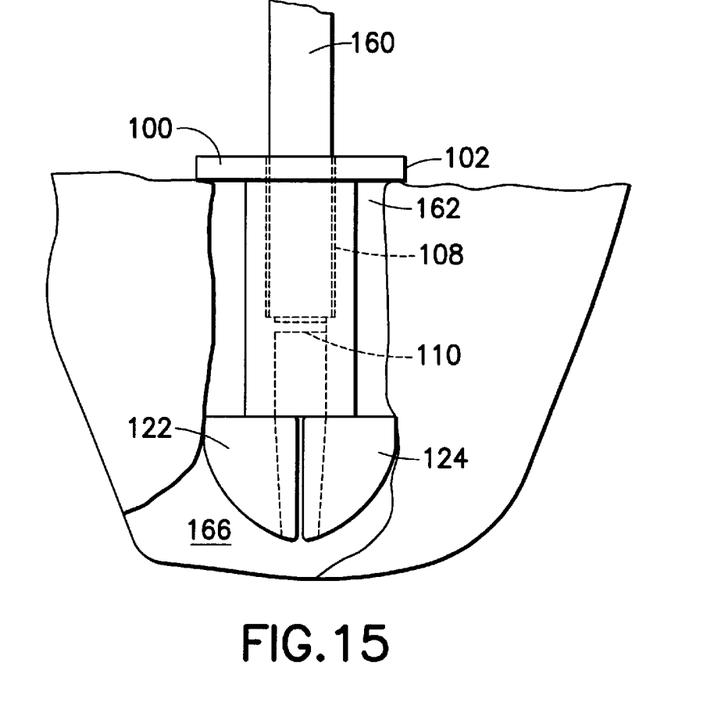

Referring now to FIGS. 14 and 15, the plug 100 is inserted as follows into the punctal opening to block the flow of tears through the nasal lacrimal duct. Particularly with reference to FIG. 14, an insertion tool 160 having substantially the same diameter as the proximal portion 112 of the axial bore 108 is positioned in the axial bore 108 of the plug 100 such that the tool 160 engages the seat 116. The body 106 of the plug is brought to the punctal opening 162. Pressure is applied to the insertion tool 160 to slowly force the plug 100 into the punctal opening 162. As the pressure is applied to the plug, the resilient portions 122, 124 of the body 106 are forced together to collapse the body 106 in on itself such that the distal dimension of the plug is decreased to facilitate insertion. Referring to FIG. 15, the plug 100 is inserted in this manner until the head 102 seats substantially flush around the punctal opening 162. Once the pressure on the tool 160 is removed, the resilient portions 122, 124 will open within the anatomical structure of the canaliculus, and the body 106 with the foldable pleat 156 will form to the shape of the lacrimal duct 166. The insertion tool 160 may then be removed from the axial throughbore 108 without dislodging the plug. The other described plugs of the invention, described both above and below, are inserted in a similar manner.

Figure 16:
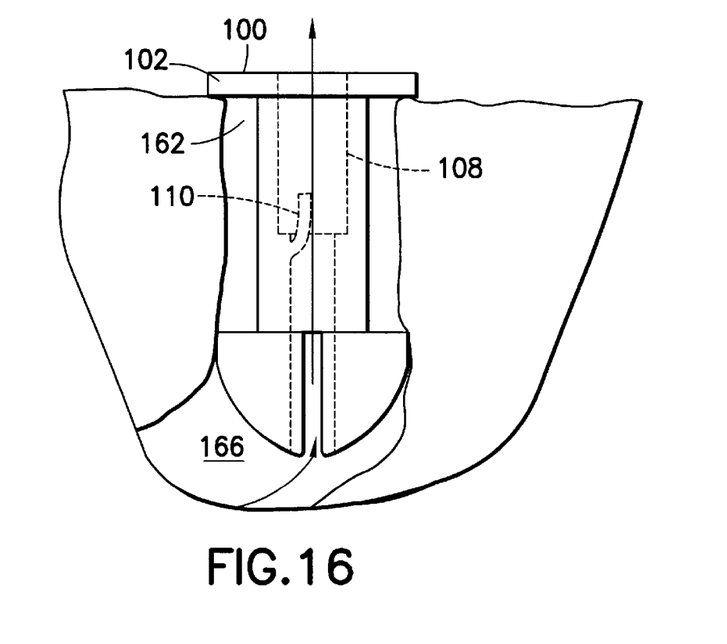
FIG. 16 generally illustrates the operation of the valve of the canalicular plug of the invention.

Once the plug 100 is seated in situ, the head 102 and preferably the body 106 of the plug will provide uninterrupted 360° occlusion of the nasal lacrimal duct 166, while any of the above described valves (e.g., valve 110) will operate to prevent tear fluid from passing completely through the axial bore 108 of the plug and into the nasal lacrimal duct 166. However, referring to FIG. 16, if a pressure differential is created such that higher pressure is provided in the nasal lacrimal duct 166 relative to the pressure provided on the head side of the plug, the valve, e.g., 110, will open to permit the pressure to be equalized and inhibit the plug from inadvertently dislodging.

Figure 17:
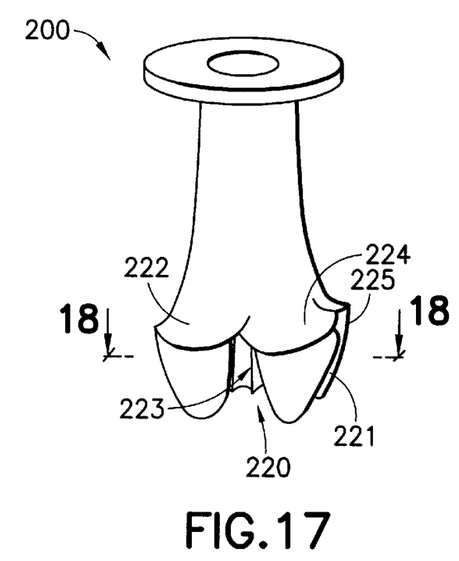
FIG. 17 is a perspective of a fifth embodiment of a canalicular plug of the invention.
Figure 18:
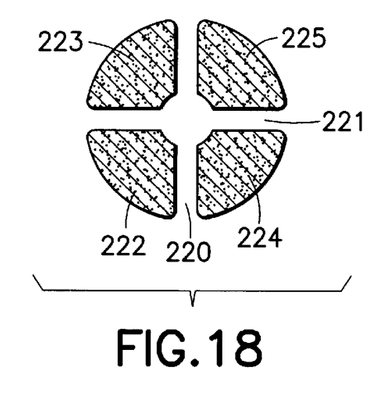
FIG. 18 is a cross-section through line 18—18 in FIG. 17.

It will also be appreciated that the distal portion of the body may also be divided into more than two resilient portions. Referring to FIGS. 17 and 18, a fifth embodiment of a plug 200, substantially similar to plug 100, is shown with four resilient portions 222, 223, 224, 225 formed by two preferably diametrical slots 220, 221. It will similarly be appreciated that three resilient portions or more than four resilient portions may also be provided to the plug 200.

Figure 19:
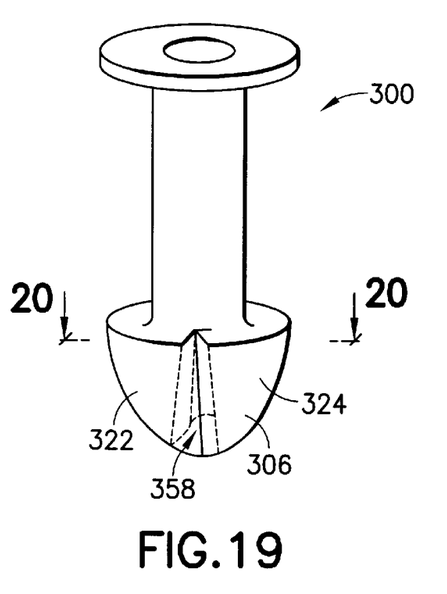
FIG. 19 is a perspective view of a sixth embodiment of a canalicular plug of the invention.
Figure 20:
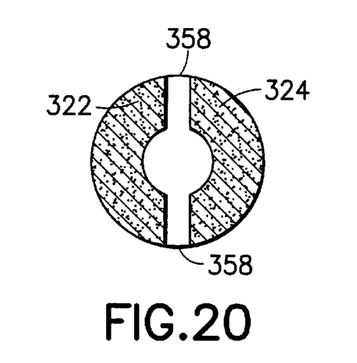
FIG. 20 is a cross-section through line 20—20 in FIG. 19.

In addition, the canalicular plug of the invention may otherwise be configured to provide 360° uninterrupted occlusion in spite of the slots which create the resilient portions. Referring to FIGS. 19 and 20, in a sixth embodiment substantially similar to the first embodiment, the body 306 of the plug 300 includes a peripheral flexible pleat ("skirt" portion) 358 which provides an uninterrupted surface between the resilient portions 322, 324.

Figure 21:
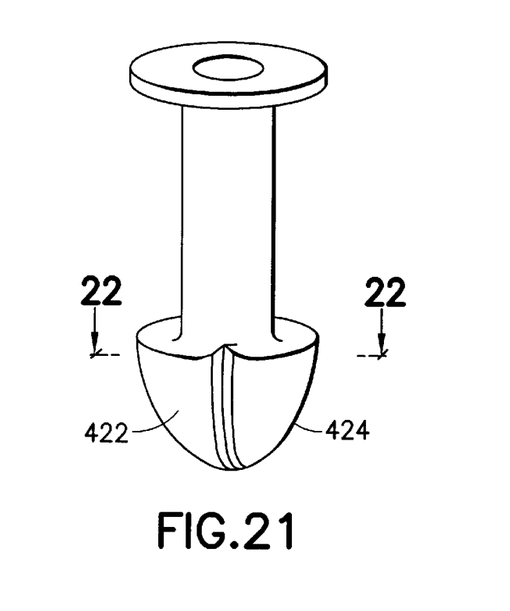
FIG. 21 is a perspective view of a seventh embodiment of a canalicular plug of the invention.
Figure 22:
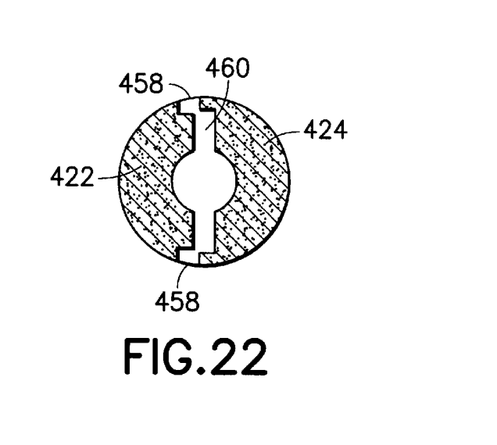
FIG. 22 is a cross-section through line 22—22 in FIG. 21.

Referring to FIGS. 21 and 22, a seventh embodiment of a canalicular plug 400 substantially similar to the embodiment shown in FIGS. 19 and 20 is illustrated. The resilient portions 422, 424 are configured such that one resilient portion 422 moves into a slot 460 within the other resilient portion 424 when compressed during insertion into the punctal opening. A peripheral flexible pleat 458 is provided between the resilient portions 422, 424 to provide an uninterrupted surface between the resilient portions 422, 424.

Figure 23:
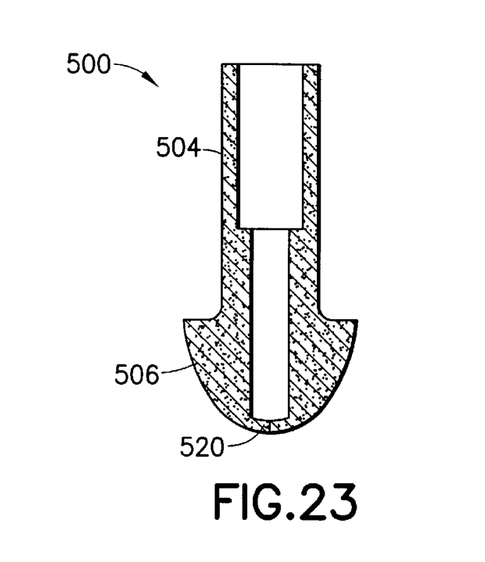
FIG. 23 is section view of an eighth embodiment of a canalicular plug of the invention.
Figure 24:
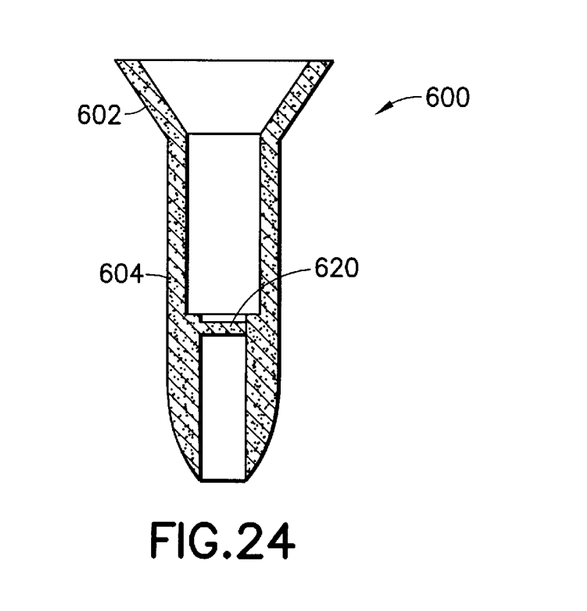
FIG. 24 is a section view of a ninth embodiment of a canalicular plug of the invention.

Moreover, while the previously described plugs have been described as including head, shaft, and body portions, it will be appreciated that to facilitate deep lacrimal insertion of a valved plug, the previously described plugs may be otherwise configured. Referring to FIG. 23, an eighth embodiment of a valved canalicular plug 500 is shown having a shaft portion 504, a body portion 506, and a valve 520, but no head portion. In FIG. 24, a ninth embodiment of a valved canalicular plug 600 is shown having a head portion 602, a shaft portion 604, and a valve 620, but no "body portion. The head portion 602 is preferably a collapsible flared proximal section which is larger than the shaft portion 604 when un-collapsed. In both of the embodiments of FIGS. 23 and 24, the valved canalicular plug is adapted for being inserted completely through the punctal opening and into the horizontal portion of the lacrimal duct and being secured therein.

Any of the plug embodiments may be provided in several sizes to provide satisfactory insertion into puncta of varying dimensions and to thereby occlude the nasal lacrimal duct. By way of example, and not by way of any limitation, the following dimensions are provided for one size of a canalicular plug, for example, the canalicular plug described as the fourth embodiment. The plug has a length of approximately 0.065 inches from head to body. The head has a diameter of approximately 0.040 inches. The shaft has a diameter of approximately 0.020 inches. The length of the plug from the proximal end of the head to the location where the shaft meets the body is approximately 0.025 inches.

There have been described and illustrated herein several embodiments of a canalicular plug for occluding the nasal lacrimal duct. While particular embodiments of the invention have been described, it is not intended that the invention be limited thereto, as it is intended that the invention be as broad in scope as the art will allow and that the specification be read likewise. Thus, while additional configurations could have been explicitly described, it is believed that such would not provide additional teaching, as all the teaching necessary for other configurations exists within the specification. Therefore, while particular valves are described for use in the plugs, it will be appreciated that other types of valves could be used as well. Moreover, while particular embodiments illustrate certain preferred locations of the valve (e.g., generally centralized within the plug or at the proximal or distal ends of the plug), it will be appreciated that in each embodiment without a distal slot, the valve may be at either a proximal, central, or distal location, and that in each embodiment with a distal slot the valve may be at either a proximal or central location. Furthermore, while some embodiments have been shown with a slot dividing the distal portion of the plug into a plurality of resilient portions, it will be appreciated that any of the embodiments not so provided could also be provided with a slot. Moreover, any slotted embodiments not described as having one or the other of an upper or peripheral pleat, could likewise be provided with such a pleat. Furthermore, while the term 'pleat' has been used to generally describe a foldable or flexible material between the resilient portions, it will be appreciated that the term is meant to include any means for connecting the resilient portions such that the resilient portions may be compressed about the slot and still provide a barrier to tear fluid. In addition, while the plug has been described as preferably being made from silicone, it will be appreciated that other suitable materials known to those skilled in the art may also be used. Furthermore, different parts of the plug can be made from different materials. Moreover, while the methods of liquid injection molding, cast molding, and transfer molding are disclosed for making the plugs, other methods known in the art can also be used. It will therefore be appreciated by those skilled in the art that yet other modifications could be made to the provided invention without deviating from its spirit and scope as so claimed.

We claim:

1. A canalicular plug for insertion into or through a punctal opening of a nasal lacrimal duct to prevent the flow of tear fluid through the nasal lacrimal duct, said canalicular plug comprising:
   a) a proximal head portion;
   b) a distal body portion sized to be received within the punctal opening;
   c) a shaft portion provided between said head portion and said body portion,
   said head portion, said body portion, and said shaft portion defining an axial throughbore which extends completely through said head portion; and
   d) a valve which substantially prevents passage of the tear fluid through said throughbore in a first direction defined by said head portion to said body portion and which permits the passage of pressurized fluid through said axial throughbore in a second direction substantially opposite said first direction,
   said head portion, said body portion, said shaft portion, and said valve being made of a flexible material.

2. A canalicular plug according to claim 1, wherein: said valve is one of a flapper valve, a duckbill valve, and a slit valve.

3. A canalicular plug according to claim 1, wherein: said valve is located at a central portion of said throughbore.

4. A canalicular plug according to claim 1, wherein: said valve is located at an end of said throughbore.

5. A canalicular plug according to claim 1, wherein: said body portion defines at least one slot which divides said body portion into at least two resilient portions which are compressible about said at least one slot.

6. A canalicular plug according to claim 5, wherein: said body portion includes a proximal surface which is substantially uninterrupted.

7. A canalicular plug according to claim 5, wherein: said body portion includes at least one of an upper pleat and a peripheral pleat between said at least two resilient portions.

8. A canalicular plug according to claim 1, wherein: said throughbore is a stepped throughbore having a proximal portion and a relatively smaller distal portion.

9. A canalicular plug according to claim 1, wherein: said valve is provided adjacent an intersection of said proximal portion and said distal portion.

10. A canalicular plug according to claim 1, wherein: said body portion is one of substantially conically shaped and substantially frustoconically shaped.

11. A canalicular plug according to claim 1, wherein: said plug is integrally molded as a single unit.

12. A canalicular plug according to claim 1, wherein: said valve is located distal of said head.

13. A canalicular plug for insertion into or through a punctal opening of a nasal lacrimal duct to substantially prevent the flow of tear fluid through the nasal lacrimal duct, said canalicular plug comprising:
   a) a first portion having a first outer diameter;
   b) a second portion having a second outer diameter smaller than said first outer diameter and sized to be received within the punctal opening, said plug defining an axial throughbore through said first and second portions; and
   c) a valve which substantially prevents the tear fluid from passing through said throughbore in a first direction defined by said first portion to said second portion and which permits the passage of fluid through said axial throughbore in a second direction opposite said first direction,
   said first and second portions being made of a flexible material.

14. A canalicular plug according to claim 13, wherein: said first portion has a substantially conical shape or substantially frustoconical shape such that said first portion tapers toward said second portion.

15. A canalicular plug according to claim 13, wherein: said first portion is compressible.

16. A canalicular plug according to claim 17, wherein: said first portion defines at least one slot which divides said first portion into at least two resilient portions which are compressible about said at least one slot.

17. A canalicular plug according to claim 18, wherein; said first portion includes a proximal surface which is substantially uninterrupted.

18. A canalicular plug according to claim 19, wherein: said first portion includes at least one of at least one upper pleat in said proximal surface and at least one peripheral pleat between said at least two resilient portions.

19. A canalicular plug according to claim 13, wherein: said throughbore is a stepped throughbore having a proximal portion sized to receive an insertion tool and a relatively smaller distal portion.

20. A canalicular plug according to claim 21, wherein: said valve is provided adjacent an intersection of said proximal portion and said distal portion.

21. A canalicular plug according to claim 13, wherein: said valve is one of a flapper valve, a duckbill valve, and a slit valve.

22. A canalicular plug according to claim 13, wherein: said valve is located at a central location within said throughbore.

23. A canalicular plug according to claim 13, wherein: said valve is located at an end of said throughbore.

24. A canalicular plug according to claim 23, wherein: said plug is integrally molded as a single unit.

25. A canalicular plug according to claim 23, wherein:

said valve is made of a flexible material.

26. In a flexible punctum plug for insertion into or through a punctal opening of a nasal lacrimal duct to prevent the flow of tear fluid through the nasal lacrimal duct, the punctum plug having a first portion having a first outer diameter, and a second portion having a second outer diameter smaller than said first outer diameter and sized to be received within the punctal opening, the improvement comprising:

a) an axial throughbore defined by plug; and
b) a valve which substantially prevents the tear fluid from passing through said axial throughbore in a first direction defined by the first portion to the second portion and which permits the passage of fluid through said axial throughbore in a second direction opposite said first direction.

* * * * *